United States Patent [19]

Anicetti et al.

[11] Patent Number: 5,411,864
[45] Date of Patent: May 2, 1995

[54] METHOD OF PURIFYING RECOMBINANT PROTEINS FROM CORRESPONDING HOST CELL PROTEINS

[75] Inventors: Vincent R. Anicetti, Pacifica; Stuart E. Builder, Belmont; Billie J. Marks, Pacifica; John R. Ogez, Union City; Eric J. Patzer, Orinda; David A. Vetterlein, Union City, all of Calif.

[73] Assignee: Genentech, Inc., South San Francisco, Calif.

[21] Appl. No.: 117,705

[22] Filed: Nov. 5, 1987

[51] Int. Cl.⁶ .............................. G01N 33/53
[52] U.S. Cl. ....................... 435/7.4; 435/7.1; 435/212; 435/240.27; 435/172.2; 530/387.1; 530/413
[58] Field of Search ............ 435/7, 212, 226, 240.27, 435/172.2, 814, 815; 436/518; 530/413, 387, 808, 809, 387.1; 935/103, 110; 434/7.1, 7.4

[56] References Cited

U.S. PATENT DOCUMENTS 4,568,488  2/1986  Lee-Huang ........................ 260/112

FOREIGN PATENT DOCUMENTS 10190711  2/1985  European Pat. Off. .
20210870  8/1985  European Pat. Off. .

OTHER PUBLICATIONS

B. D. Davis et al, Microbiology, Third Edition, Harper & Row Publishers, 1980, pp. 525 and 527.
Köhler et al, Nature vol. 256, Aug. 7, 1975, pp. 495–497., "Continuous Cultures Of Fused Cells Secreting Antibody Of Predefined Specificity".
Sevier, et al., Clin. Chem 27/11, 1981, pp. 1797–1806, "Monoclonal Antibodies In Clinical Immunology".
Cajot et al., Thrombosis Research 46, 141 (1987).
Matsuo et al., Thrombosis Research 36, 517 (1984).
Reagan et al, Hybridoma 4, 83 (1985); Thrombosis Research 40, 1 (1985).
Verheijen et al., The EMBO Journal 5, 3525 (1986).

Primary Examiner—Christine M. Nucker
Assistant Examiner—Laurie Scheiner
Attorney, Agent, or Firm—Walter H. Dreger

[57] ABSTRACT

A method for purifying a recombinant protein, e.g. human tissue plasminogen activator (t-PA) from a corresponding endogenous protein of the host cell, e.g. Chinese hamster t-PA, is disclosed. The method comprises contacting a fluid containing the recombinant protein with antibodies specifically binding the corresponding endogenous protein. Monoclonal antibodies directed against and an assay for Chinese hamster t-PA are also disclosed.

17 Claims, No Drawings

METHOD OF PURIFYING RECOMBINANT PROTEINS FROM CORRESPONDING HOST CELL PROTEINS

FIELD OF THE INVENTION

The present invention is directed to a method of purifying recombinant proteins from related host cell proteins. The invention is also directed to the monoclonal antibodies used in the purification, and to an assay for the related host cell protein.

BACKGROUND OF THE INVENTION

The production of recombinant proteins in eukaryotic cells may result in the co-purification of related host cell proteins. The production of human tissue plasminogen activator (t-PA) in Chinese hamster ovary (CHO) cells may therefore result in the co-purification of Chinese hamster plasminogen activator(s) (PA) produced by CHO cells (CHO-PA).

Human t-PA is an extremely important new biological pharmaceutical agent shown to have great promise in the treatment of vascular diseases due to its high specificity and potent ability to dissolve blood clots in vivo. Accordingly, t-PA has been hailed by medical science as one of the most impressive new agents of recent history for the treatment of vascular occlusive disease, and in particular, heart disease. For these and other reasons, t-PA will likely revolutionize the clinical management of serious vascular disease.

Human t-PA protein, as well as the underlying gene sequences which code for it, has been the subject of numerous scientific disclosures over the previous few years. For example, its isolation from natural sources has been described by Rijken et al., *J. Biol Chem.* 256, 7035 (1981) and European Patent Application Publication No. 041766. Moreover, a patent and various patent applications have been published detailing the structure and isolation of t-PA from recombinant sources (see, e.g., UK Patent 2,119,804; and European Patent Application Publication No. 093619).

Monoclonal antibodies which bind to human t-PA but do not bind to swine t-PA have been made, for example European Patent Application 190711 relates to monoclonal antibodies which are specific to human tissue plasminogen activator obtained from a tissue cultured liquor of normal human tissue derived cells. Use of these monoclonal antibodies in the purification of human t-PA and in an assay for human t-PA, are disclosed. Monoclonal antibodies X-21 and X-23 did not cross react with urokinase or plasminogen activator extracted from swine heart.

European Patent Application 210870 discloses an affinity reagent containing an immobilized Kunitz inhibitor which is produced in the seeds of Erythrina latissima and other Erythrina plants. The affinity reagent is said to be capable of separating human cell derived t-PA and host cell derived plasminogen activator from each other.

Verheijen et al., *EMBO Journal*, Vol. 5, No. 13, pp 3525–3530 (1986) disclose the presence of CHO-PA when expressing human t-PA in CHO cells.

It is an object of the subject invention to provide a method of purifying recombinant protein, e.g. human t-PA to a very high degree by substantial reduction of the corresponding endogenous protein of the host cell, e.g. Chinese hamster plasminogen activator.

It is a further object of the invention to provide monoclonal antibodies to Chinese hamster plasminogen activator.

It is a further object of the invention to provide an assay for Chinese hamster plasminogen activator.

Other objects, features and characteristics of the present invention will become more apparent upon consideration of the following description and the appended claims.

SUMMARY OF THE INVENTION

The subject invention relates to a method for purifying a recombinant protein from a corresponding endogenous protein of the host cell comprising the steps of contacting fluid containing recombinant protein with antibodies specifically binding the corresponding endogenous protein, and recovering said recombinant protein. The invention also relates to an assay for the corresponding endogenous protein and to the monoclonal antibodies specifically binding the corresponding endogenous protein.

DETAILED DESCRIPTION OF THE INVENTION

It has been discovered that recombinant proteins can be isolated from related host cell proteins by immunopurification using monoclonal antibodies. The invention relates to a method wherein fluid obtained from culturing a host cell expressing a recombinant protein as well as the corresponding endogenous proteins of the host cell is contacted with antibodies specifically binding the corresponding endogenous protein. The monoclonal antibodies bind the corresponding endogenous protein and the human recombinant protein is then recovered. More specifically, when human tissue plasminogen activator (t-PA) is produced through recombinant means in Chinese hamster ovary (CHO) cells, the human t-PA can be isolated from the endogenous Chinese hamster plasminogen activator(s) (CHO-PA) by using the method of the subject invention.

The subject invention provides a method wherein fluid obtained from culturing CHO cells expressing human t-PA as well as Chinese hamster plasminogen activator (PA) is contacted with antibodies, advantageously monoclonal antibodies, which bind Chinese hamster PA. The human t-PA is not bound and a separation is effected. The subject invention also relates to monoclonal antibodies specific for Chinese hamster PA, and to an assay for detecting the presence of Chinese hamster PA.

The method of the subject invention is preferable to the use of antibodies specifically binding human t-PA, since the latter method requires purification means, e.g. a column, several orders of magnitude larger than the method of the subject invention since the concentration of human t-PA is several orders of magnitude larger than the concentration of CHO-PA. In addition, in the method of the subject invention, there is no treatment of the product of interest with denaturing agents or other harsh conditions, to elute the product from the antibody.

As used herein, the terms "human tissue plasminogen activator", "human t-PA" or "t-PA" denotes human extrinsic (tissue type) plasminogen activator, produced, for example, from natural source extraction and purification (see Collen et al., supra.), and by recombinant cell culture systems as described herein. Its sequence and characteristics are set forth, for example, in European Patent Application Publication No. 93619, (published 9 November 1983) based upon a first filing on 5 May 1982, incorporated herein by reference. See also European Patent Application Publication No. 41766 (published 16 Dec. 1981) based upon a first filing of 11 Jun. 1980 and Rijken et al., *Journal of Biol. Chem.* 256, 7035 (1981), also incorporated herein by reference. The terms likewise cover biologically active human tissue plasminogen activator equivalents, differing in one or more amino acid(s) in the overall sequence, or in glycosylation patterns. Further, the terms as used in this application are intended to cover substitution, deletion and insertion amino acid variants of t-PA or post translational modifications.

Human t-PA can be produced by transfecting a variety of eukaryotic cells, such as baby hamster kidney cells, myeloma cells, insect cells, 3T3 cells, and other transfectable cells having a useful post-transfectional life. Advantageously, Chinese hamster ovary (CHO) cells are used.

In accordance with this invention, monoclonal antibodies specifically binding CHO-PA were isolated from continuous hybrid cell lines formed by the fusion of antigen-primed immune lymphocytes with myeloma cells. In another embodiment of the invention, polyclonal antibodies specifically binding CHO-PA are used.

Monoclonal antibodies are highly specific, being directed against a single antigenic site. Furthermore, in contrast to conventional antibody (polyclonal) preparations which typically include different antibodies directed against different determinants (epitopes), each monoclonal antibody is directed against a single determinant on the antigen. Monoclonal antibodies are useful to improve the selectivity and specificity of diagnostic and analytical assay methods using antigen-antibody binding. A second advantage of monoclonal antibodies is that they are synthesized by the hybridoma culture, uncontaminated by other immunoglobulins. Monoclonal antibodies may be prepared from supernatants of cultured hybridoma cells or from ascites induced by intra-peritoneal inoculation of hybridoma cells into mice.

The hybridoma technique described originally by Kohler and Milstein, *Eur. J. Immunol.* 6.511 (1976) has been widely applied to produce hybrid cell lines that secrete high levels of monoclonal antibodies against many specific antigens.

The route and schedule of immunization of the host animal or cultured antibody producing cells therefrom are generally in keeping with established and conventional techniques for antibody stimulation and production. Applicants have employed mice as the test model although it is contemplated that any mammalian subject including human subjects or antibody producing cells therefrom can be manipulated according to the processes of this invention to serve as the basis for production of mammalian, including human, hybrid cell lines.

After immunization, immune lymphoid cells are fused with myeloma cells to generate a hybrid cell line which can be cultivated and subcultivated indefinitely, to produce large quantities of monoclonal antibodies. For purposes of this invention, the immune lymphoid cells selected for fusion are lymphocytes and their normal differentiated progeny, taken either from lymph node tissue or spleen tissue from immunized animals. Applicants prefer to employ immune spleen cells, since they offer a more concentrated and convenient source of antibody producing cells with respect to the mouse system. The myeloma cells provide the basis for continuous propagation of the fused hybrid. Myeloma cells are tumor cells derived from plasma cells.

It is possible to fuse cells of one species with another. However, it is preferred that the source of immunized antibody producing cells and myeloma be from the same species.

The hybrid cell lines can be maintained in culture in vitro in cell culture media. The cell lines of this invention can be selected and/or maintained substantially indefinitely in a composition comprising the continuous cell line in the known hypoxanthine-aminopterin-thymidine (HAT) medium. In fact, once the hybridoma cell line is established, it can be maintained on a variety of nutritionally adequate media. Moreover the hybrid cell lines can be stored and preserved in any number of conventional ways, including freezing and storage under liquid nitrogen. Frozen cell lines can be revived and cultured indefinitely with resumed synthesis and secretion of monoclonal antibody. The secreted antibody is recovered from tissue culture supernatant by conventional methods such as precipitation, ion exchange, affinity chromatography, or the like.

As an alternative to the cell fusion technique, EBV immortalized B cells are used to produce the monoclonal antibodies of the subject invention. Other methods for producing monoclonal antibodies such as recombinant DNA, are also contemplated.

Described herein are serological methods for determining the presence of CHO-PA. Essentially, the processes of this invention comprise incubating or otherwise contacting the sample to be tested with monoclonal antibodies and detecting the presence of a reaction product. Those skilled in the art will recognize that there are many variations of these basic procedures. These include for example, RIA, ELISA, precipitation, agglutination, complement fixation and immunofluorescence. In the presently preferred procedures, the monoclonal antibodies are appropriately labeled. A convenient label for this assay is a radioactive isotope, particularly $^{125}I$. However, enzymes particularly peroxidase are also useful.

The antibody is labeled with a radioactive element, an enzyme or a fluorescent material. The radiolabel can be detected by any of the currently available counting procedures. The preferred isotope labels are $^{14}C$, $^{131}I$, $^{125}I$, $^{3}H$ and $^{35}S$. The enzyme label can be detected by any of the currently utilized colorimetric, spectrophotometric, fluorospectro-photometric or gasometric techniques. The enzyme is combined with the antibody with bridging molecules such as carbodiimides, periodate, diisocyanates, glutaraldehyde and the like. Many enzymes which can be used in these procedures are known and can be utilized. Examples are peroxidase, alkaline phosphatase, β-glucuronidase, β-D-glucosidase, β-D-galactosidase, urease, glucose oxidase plus peroxidase, galactose oxidase plus peroxidase and acid phosphatase. Fluorescent materials which may be used include, for example, fluorescein, rhodamine and auramine. Various labeling techniques are described in Morrison, *Methods in Enzymology* 32b, 103 (1974), Syvanen et al., *J. Biol. Chem.* 284, 3762 (1973) and Bolton and Hunter, *Biochem J.* 133, 529(1973) hereby incorporated by reference.

The following examples are offered to more fully illustrate the invention, but are not to be construed as limiting the scope thereof.

EXPERIMENTAL

I. MONOCLONAL ANTIBODIES AGAINST CHO-PA

A. Immunization Procedure

A female Balb/c mouse was immunized over a period of 12 weeks with protein solutions substantially enriched in Chinese hamster plasminogen activator purified from host cell lacking the human t-PA geneo There were five injections each consisting of approximately 30 µg. The initial injection was emulsified with complete Freund's adjuvant and administered in one subcutaneous site(s). The second injection given 1.5 weeks later was emulsified with incomplete Freund's adjuvant and half was administered subcutaneously and half intraperitoneally. The remaining three injections were given on weeks 3, 6 and 12 in phosphate buffered saline (PBS) administered in one intraperitoneal site.

B. Fusion and Selection of CHO-PA Specific Monoclonal Antibodies

The spleen from the immunized mouse was removed on week 13 and spleen cells were fused with the mouse myeloma cell line NP3X63-Ag8.653 using the general procedures of S. Fazekas, de St. Groth and D. Scheidegger (*J. Immunol. Methods* 35, 1 (1980)) and Lane, R. D. (*J. Immunol. Methods* 81 223 (1985)). The fused cells were distributed into ten microtiter plates each containing 96 wells. Each well was screened for specific antibody production using differential reactivity in two ELISA's (enzyme linked immunoadsorbant assays). One ELISA specifically detected antibodies against CHO-PA and the second detected antibodies that cross-reacted with recombinant human tissue plasminogen activator (t-PA).

For the CHO-PA specific ELISA 50 ng/mL of CHO-PA in 50 mM carbonate buffer pH 9.6 was adsorbed to microtiter wells overnight at 4° C. The antigen was removed and the wells were washed with phosphate buffered saline containing 0.05% Tween 20 (PBS-TW20). Further adsorption was inhibited by adding 1% gelatin in Tris buffered saline (TBS; 0.15M NaCl, 0.05M Tris pH 7.4) to the wells and incubating for 1 h at room temperature. After aspirating the contents, 0.05 mL of PBS containing 5 mg/mL of bovine serum albumin (BSA) was added to each well followed by 0.1 mL of supernatant from each well of the fusion plate. After incubating for 2 h at room temperature, the contents of each well were aspirated and washed three times with PBS-TW20. Goat anti-mouse immunoglobulin coupled to horse radish peroxidase was added followed by incubation for 1 h at room temperature. The wells were washed three times with PBS-TW20, and O-phenylene diamine was added as substrate followed by incubation for 30 minutes at room temperature. The reaction was stopped with 2.5M $H_2SO_4$ and the absorbance of each well was read at 492 nm.

The human t-PA specific ELISA differed from the CHO-PA specific ELISA in the first step. 200 ng/mL of t-PA in 50 mM carbonate buffer at pH 9.6 was adsorbed to microtiter wells overnight at 4° C. The remainder of the ELISA was identical.

Approximately 5% of the total wells were reactive only with CHO-PA, and 3% reacted with CHO-PA and human t-PA. Hybridoma cells from wells containing CHO-PA specific antibodies were expanded and cloned by limiting dilution (Oi, V.T. and Herzenberg, L. A. 1980. Immunoglobin-Producing Hybrid Cell Lines p. 351-372, in *Selected Methods in Cellular Immunology*, Mishell, B.B. and Shiigi, S.M. (eds.) W. H. Freeman and Co.). Large quantities of specific monoclonal antibodies were produced by cell culture of the hybridoma cells or by injection of hybridoma cells in mice thereby producing ascites tumors.

II. CHO-PA SPECIFIC ELISA

The subject invention also relates to a monoclonal antibody based assay for the quantitation of Chinese hamster ovary cell plasminogen activator (CHO-PA). Immunoassays using specific monoclonal antibodies provide one approach to the quantitation of small amounts of such a protein impurity which exists in the presence of a vast excess of the biochemically related recombinant product. An ELISA that specifically detects CHO-PA and not human t-PA was developed using two CHO-PA specific monoclonal antibodies (MAb) designated 335 and 361. These MAbs were selected based on their capacity to bind $^{125}$I-labeled CHO-PA, their minimal cross-reactivity with human t-PA and the fact that they each bound to a different epitope on CHO-PA. These antibodies demonstrated positive reactivity with CHO-PA, but did not react with human t-PA which had been depleted of CHO-PA. The capacity of each MAb to bind CHO-PA was assessed by determining the amount of $^{125}$I-labeled CHO-PA that bound to each MAb that was non-specifically adsorbed to microtiter wells. To establish that MAbs 361 and 335 bound to different epitopes the $^{125}$I-labeled CHO-PA was pre-incubated with one MAb in solution before adding the mixture to the microtiter well containing the second MAb. If the first MAb did not inhibit the $^{125}$I-labeled CHO-PA from binding to the second MAb, they were considered to be against different epitopes.

The cross-reactivity of the MAbs with human t-PA was assessed by ELISA. 100 ng of either CHO-PA or t-PA was adsorbed to microtiter wells. Various dilutions of the purified MAbs were reacted with each antigen and the amount of antibody bound was determined using a horseradish peroxidase conjugated goat anti-mouse antibody. The cross-reactivity was calculated from the dilutions that resulted in the same absorbance against CHO-PA and human t-PA for a given MAb.

On the basis of these results a CHO-PA specific "sandwich" ELISA was developed using MAb 335 to coat microtiter Wells and MAb 361 was conjugated to horseradish peroxidase to detect bound CHO-PA. The assay standard is cloned CHO-PA which was expressed in CHO cells. The assay is accurate, precise, and specific for the detection and quantitation of CHO-PA. The sensitivity (limit of detection) of this ELISA is about 3.9 ng/mL of CHO-PA and the cross-reactivity with human t-PA is less than about 0.002 percent.

To examine the specificity of the assay itself, human t-PA containing CHO-PA was passed over a column of sepharose 4B coupled with monoclonal antibody 341 which is specific for CHO-PA. The material which flowed through this column represented human t-PA which had been depleted of CHO-PA and therefore was an appropriate sample for the determination of assay specificity. Antibody 341 is directed to a different antigenic determinant on CHO-PA than either antibody 335 or 361. Thus, purification of human t-PA by this antibody avoids purification and subsequent measurement of CHO-PA by the same antibody (i.e., directed to the same antigenic determinant). Table 1 demonstrates the assay values obtained for the immunoaffinity purification of CHO-PA from human t-PA using this antibody.

TABLE 1

PURIFICATION OF HUMAN t-PA FROM CHO-PA
USING MONOCLONAL ANTIBODY COLUMN (#341)[a]

1A. Reduction of CHO-PA Levels in Column Flowthrough[b]

| Flowthrough Fraction No. | CHO-PA (percent of initial concentration) | Human t-PA (percent of initial concentration) | Fold Reduction in CHO-PA levels |
|---|---|---|---|
| 6 | 0.38 | 74.0 | 193 |
| 30 | 0.77 | 69.2 | 90 |
| 64 | <.05 | 8.8 | >184 |

1B. Elution of CHO-PA from Monoclonal Antibody Column with 0.2 M glycine-HCl, pH 2.4[c]

| Sample | CHO-PA (μg) | Human t-PA | Percent Purity CHO-PA |
|---|---|---|---|
| glycine-HCl Column Eluate | 22.6 | 1.2 | 95 |

[a]The solution containing human t-PA (100 mL) was passed through the column and fractions (1.67 mL each) of this flowthrough were collected. At fraction 51 washing began with PBS containing 1 M NaCl. At fraction 100 elution began with glycine-HCl and the fraction size increased to 2.5 mL.
[b]Three representative fractions of the flowthrough were tested for CHO-PA. Human t-PA concentration was determined by absorbance at 280 run assuming an extinction coefficient of 1.9 for human t-PA.
[c]The specific removal of CHO-PA was shown by assay of the glycine-HCl eluate for CHO-PA and human t-PA. Human t-PA content was determined by monoclonal antibody based ELISA for human t-PA.

It is apparent from this data that the level of CHO-PA has been reduced by approximately 100 fold or more, as determined by comparison of the percentage of CHO-PA in the starting material to that in the peak flowthrough fraction. Further, the absorbed CHO-PA that was eluted from this column with 0.1M glycine-HCL or 3M NaSCN ranged from 67 to 94 percent purity, with the glycine-HCL pool containing 95 percent CHO-PA. If a conservative approach is taken, which assumes all of the reactivity in the flowthrough is the result of cross reactivity in the assay, this amounts to a cross reactivity of at most 0.002 percent.

To determine accuracy, recombinant CHO-PA was spiked into a sample of rt-PA which had been depleted of endogenous CHO-PA by immunoaffinity chromatography. Spike recovery analysis of CHO-PA added independently at concentrations of 11.5 and 31.5 ng/mL demonstrated mean recoveries of 103 and 105 percent respectively. These data demonstrate the assay can accurately detect CHO-PA in the presence of human t-PA.

TABLE 2

RECOVERY OF CHO-PA ADDED TO HUMAN t-PA

| Endogenous CHO-PA ng/mL | CHO-PA Added ng/mL | CHO-PA Expected[a] ng/mL | CHO-PA Recovered ng/mL | Percent Recovery[b] ng/mL |
|---|---|---|---|---|
| 33.7 | 11.5 | 45.2 | 46.5 | 103 |
| 33.7 | 31.5 | 65.2 | 68.5 | 105 |

[a]Expected = Endogenous + Added
[b]Recovery = Recovered/Expected × 100

III. CHO-PA Monoclonal Antibody Selection for CHO-PA Removal in the t-PA Manufacturing Process In modeling experiments immobilized monoclonal antibody #354 lowered CHO-PA levels greater than about 100 fold in a single column pass. The antibody is stable to several different immobilization chemistries, and harsh washing conditions. Appropriately configured MAb 354 affinity columns can be re-used many times to remove CHO-PA from recombinant human t-PA harvest fluids without significant losses in binding activity. Thus, a MAb 354 column is suitable for use as a reusable biospecific filter for removal of trace levels of CHO-PA from human t-PA as shown below.

Eight different ascites fluids directed against CHO-PA were tested by an ELISA for direct binding to CHO-PA coat. Polystyrene ELISA plates were passively coated with 1 μg of affinity purified CHO-PA per well in carbonate buffer pH 9.6 overnight at 4° C. then blocked with 0.5% BSA in PBS. Protein A purified MAbs were titered and ranked with respect to CHO-PA binding. Each MAb was diluted 1/200 in the first well followed by serial two fold dilutions and incubated at room temperature for 2 hours. Goat anti-mouse IgG HRP conjugate was then employed to detect bound antibody (incubated for 1 hour at RT at 1/40,000 dilution). Color development was accomplished by addition of OPD substrate for 30 minutes and stopping the reaction by addition of acid. $OD_{492}$ was then read using an ELISA plate reader. When ELISA titers were adjusted for concentration the following rankings were obtained: CHO-PA MAb 354=359=361=335 (were not distinguishable) but bound more tightly to CHO-PA coated plates than 327>360>341>325.

ELISA based elution studies were also performed. Analysis of the elution behavior for the various MAbs was evaluated with respect to several buffers including pH 3.0 and pH 2.0 acetic acid containing low (0.15M) and high (1.5M) NaCl; sodium thiocyanate 3M, pH 8.5, pH 10.0; 2M sodium thiocyanate pH 8.5 and pH 5.2; 2.0M $MgCl_2$, pH 5.2; and glycine pH 5.2 (all potential affinity column eluants). The monoclonal antibodies showed different patterns or sensitivity to these reagents. For example, 354 and 361 were easily removed from plate coated CHO-PA under acid conditions and 359 and 361 were resistant to 3M NaSCN, pH 8.5 buffer. The 354 MAb was removed by a broad spectrum of eluants.

In order to define the best MAb of those made for CHO-PA removal from recombinant t-PA harvest fluids, 7 different CHO-MAbs were immobilized to CNBr activated Sepharose CL 4B (a generic procedure for MAb immobilization) at a coupling level of 1 mg per ml resin. Unreacted sites were blocked with ethanolamine. Seven separate small columns were packed each containing 1 ml of affinity resin. The affinity columns were then pre-washed with acetic acid 0.1M, 0.15M NaCl, pH 3.0 followed by PBS pH 7.4 containing 0.5M L-arginine (PBS). Each column was then tested for the ability to remove CHO-PA contaminant from cell culture derived t-PA harvest fluid. Twenty ml of t-PA harvest fluid was loaded onto each column, and each was washed with 30 column volumes of PBS. The t-PA harvest fluid flow through was assayed for CHO-PA after chromatography. The various affinity columns were ranked on the basis of the amount of CHO-PA remaining in the flow through (Table 3). In a control experiment t-PA harvest fluid was applied to an ethanolamine blocked Sepharose CL 4B column containing no antibody. As shown below the MAb 354 was superior with respect to CHO-PA removal. It is also important to note that the acetic acid eluants from each column were analyzed by SDS gel analysis and compared to t-PA harvest fluid and purified recombinant CHO-PA standards. Eluted protein obtained from most of the affinity columns co-migrated with the recombinant CHO-PA standard, indicating that the MAbs tested were highly selective for CHO-PA trace contaminant and were not cross-reactive with human t-PA.

TABLE 3

RANKING OF COLUMNS

| Ranking (Best 1st) | Immobilized CHO-PA MAb | Percent of Total CHO-PA in Flow Through |
|---|---|---|
| 1 | 354 | 0.3 |
| 2 | 361 | 0.61 |
| 3 | 335 | 0.86 |
| 4 | 359 | 3.2 |
| 5 | 360 | 9.4 |
| 6 | 341 | 13.2 |
| 7 | 327 | 54.6 |
| control | ethanolamine blocked | 100 |

Evidence for 354 Mab stability to different immobilization chemistries, chaotropic eluants, low pH and multiple column reuses was obtained in three separate types of chromatography experiments. First, MAb 354 was immobilized to CNBr activated Sepharose CL 4B and used in affinity column experiments to purify recombinant CHO-PA from cell culture fluids. MAb 354 appeared to be stable for multiple purification cycles where NaSCN 2M, pH 8.5 and pH 3.0 glycine was employed for CHO-PA elution and column regeneration.

Second, Mab 354 was immobilized on Sepharose 6 Fast Flow which had been activated by carbonyl diimidazole by the method of Bethell et al. (J. Biol. Chem. 254 (8), pp 2572–2574, 1979). This resin was used to remove CHO-PA from partially purified preparations of human t-PA. Levels of CHO-PA were reduced by at least 100 fold and the resin showed no change in function over at least 60 cycles in which 3M NaSCN, pH 8, was used as a regenerant.

Third, MAb 354 was immobilized to N-hydroxysuccinimide activated AffiPrep resin from BioRad and was tested at 4° C. for ability to remove CHO-PA derived from t-PA harvest fluid. The reuse capability of the 354 affinity column was also tested. Monoclonal antibody was coupled at 3 mg/ml of resin. Column flow rate was fixed at 20 column volumes per hour. The column was loaded with 25 column volumes of unconcentrated t-PA harvest fluid, washed with 20 column volumes of PBS buffer, regenerated with 5 column volumes of 2.0M Guanidine HCL, in 0.2M acetic acid pH 3.0 and then reequillibrated with 10 column volumes of PBS. Levels of CHO-PA in starting t-PA harvest fluids were lowered greater than 100 fold in a single column pass with no detectable loss in binding activity after 100 column reuses. Thus, 354 MAb was successfully employed as a reusable biospecific filter for CHO-PA removal under simulated process conditions.

Although the embodiments exemplified relate to separation of CHO-PA-from human t-PA, the method of the subject invention can be used in all cases where a transfected host cell produces an endogenous protein which corresponds to a recombinant protein and, antibodies specifically binding the corresponding endogenous protein can be obtained. Further, while the invention has been described in what is considered to be its preferred embodiments, it is not to be limited to the disclosed embodiments, but on the contrary, is intended to cover various modifications and equivalents included within the spirit and scope of the appended claims, which scope is to be accorded the broadest interpretation so as to encompass all such modifications and equivalents.

What is claimed is:

1. A method for purifying human tissue plasminogen activator derived from Chinese hamster ovary cells comprising the steps of:
   contacting a fluid containing human tissue plasminogen activator with antibodies specifically binding Chinese hamster plasminogen activator, and
   recovering said human tissue plasminogen activator.

2. A method as in claim 1 wherein said antibodies are monoclonal antibodies which bind one antigenic determinant of Chinese hamster plasminogen activator.

3. A method as in claim 1 wherein said antibodies specifically bind two or more antigenic determinants of Chinese hamster plasminogen activator.

4. A method as in claim 1 wherein said contacting step comprises passing a fluid containing human plasminogen activator through a chromatographic bed having said antibodies immobilized thereon.

5. A method as in claim 1 wherein said fluid containing human tissue plasminogen activator is a culture medium obtained by culturing Chinese hamster ovary cells capable of expressing human tissue plasminogen activator.

6. A method as in claim 2 wherein said monoclonal antibodies are murine monoclonal antibodies.

7. A monoclonal antibody specific for Chinese hamster plasminogen activator.

8. A monoclonal antibody as in claim 7 which is a murine monoclonal antibody.

9. A hybridoma capable of producing a monoclonal antibody specific for Chinese hamster plasminogen activator.

10. A hybridoma as in claim 9 which is a murine hybridoma.

11. A process for assaying for Chinese hamster plasminogen activator in the presence of human tissue plasminogen activator comprising the steps of:
   providing antibodies specifically binding said Chinese hamster plasminogen activator of a host cell, said antibodies not binding said human tissue plaminogen activator;
   contacting a fluid which may contain both said Chinese hamster plasminogen activator and said human tissue plasminogen activator with said antibodies; and
   determining the extent of said Chinese hamster plasminogen activator bound to said antibodies.

12. A process as in claim 11 wherein said providing, contacting and determining steps comprise an ELISA assay.

13. A process as in claim 11 wherein said antibodies are monoclonal antibodies.

14. A method for purifying human tissue plasminogen activator as a protein of recombinant expression in a host cell from Chinese hamster plasminogen activator of said host cell comprising the steps of:
   contacting a fluid that may contain said human tissue plasminogen activator and said Chinese hamster plasminogen activator with antibodies specifically binding said Chinese hamster plasminogen activator to form a complex thereof; and
   recovering said human tissue plasminogen activator from said complex.

15. A method as in claim 14 wherein said antibodies are monoclonal antibodies.

16. A process according to claim 11 wherein said fluid is medium of cultured recombinant Chinese hamster ovary cells.

17. The method according to claim 14 wherein said fluid is medium of cultured recombinant Chinese hamster ovary cells.

* * * * *

UNITED STATES PATENT AND TRADEMARK OFFICE
CERTIFICATE OF CORRECTION

PATENT NO. : 5,411,864

DATED : May 2, 1995

INVENTOR(S) : Anicetti et al.

It is certified that error appears in the above-indentified patent and that said Letters Patent is hereby corrected as shown below:

Column 3, line 45, delete "6.511" and insert therefor --6, 511--.

Column 5, line 26, delete "81 223" and insert therefor --81, 223--.

Column 9, line 56, delete "PA-from" and insert therefor --PA from--.

Signed and Sealed this

Eighteenth Day of July, 1995

Attest:

BRUCE LEHMAN

Attesting Officer      Commissioner of Patents and Trademarks